US00PP13986P29

(12) United States Plant Patent
Sterrett

(10) Patent No.: US PP13,986 P2
(45) Date of Patent: Jul. 15, 2003

(54) STRAWBERRY PLANT NAMED 'NB-1'

(76) Inventor: Jerry Sterrett, 18690 Avenida Bosque, Murrieta, CA (US) 92562

( * ) Notice: Subject to any disclaimer, the term of this patent is extended or adjusted under 35 U.S.C. 154(b) by 0 days.

(21) Appl. No.: 09/676,944

(22) Filed: Oct. 2, 2000

(51) Int. Cl.[7] ..... A01H 5/00
(52) U.S. Cl. ..... Plt./208
(58) Field of Search ..... Plt./208

*Primary Examiner*—Bruce R. Campell
*Assistant Examiner*—Anne Marie Grünberg
(74) *Attorney, Agent, or Firm*—Mary Jo Redman; Calif Tervo

(57) ABSTRACT

A new and distinct winter-planted short-day-type cultivar of strawberry, known as 'NB-l', is adapted to the growing areas of the southern coast of California. The plant produces early, large, smooth, and uniformity-shaped fruit. Plant materal can be planted early with minimum chill. Plants are moderately more vigorous that comparative variety plants.

5 Drawing Sheets

BACKGROUND OF THE INVENTION

The new variety of strawberry plant was selected as a seedling from a controlled breeding plot in Vista, Calif. in or about April 1998. The seedling was selected from among plants germinated from open-pollinated seed gathered from *Fragaria×ananassa* Duchesne 'Pajaro' plants, also known as 'Pajaro' strawberry. Because the seed was open-pollinated, the other parent variety is not known.

The selected seedlings was grown and asexually propagated from stolons at a nursery near sea level in Bonsall, in San Diego county in California. Further generations of plants were propagated from stolons at a high elevation nursery in Mcdoel, Calif., and extensively tested.

This propagation and testing has confirmed that the new variety has a desirable combination of traits, which remain true to type through successive generations of asexual propagation. Propagation by use of both stolons and microtissue culture the been successful, though other means of asexual propagation might be used as well.

The parent variety, 'Pajaro', is described in U.S. Plant Pat. No. 4,538. 'Pajaro' has been grown on the northern coast of California in a system whereby plants were propagated and held in cold storage until being planted out in summer. The new variety, in contrast, was selected for fall planting and winter fruiting. Compared to 'Pajaro', the new variety requires fewer hours of chilling and produces fruit earlier in the season. The new variety produces conical fruit with a meaning mass of 24.2 grams; 'Pajaro' produces wedge-shaped fruit with a typical mass of 22.2 grams. The average total yield per plant of the new variety is 1376 grams of fruit per plant; a typical yield for 'Pajaro' is 1127 grams. 'Pajaro' and the new variety of strawberry were not directly compared in side-by-side testing because 'Pajaro' does not thrive in coastal southern California, the environment for which the new variety was selected, and does not set fruit at the same season as the new variety.

SUMMARY OF THE INVENTION

The present invention relates to a new and distinct variety of strawberry plant, *Fragaria×ananassa* Duchesne 'NB-1'. The new variety is distinguished from older varieties by a combination of traits, including vigorous growth habit; low chill requirement; ability in winter to flower and set fruit; large conical fruit; good taste, texture, and color of the fruit; and good cold storage qualities of the fruit. The new variety is well adapted for commercial use in coastal southern California.

COMPARISON TO CLOSEST VARIETY

The new variety is believed to be similar in characteristics to 'Camarosa' (U.S. Plant Pat. No. 8,708, filed Apr. 1, 1993). 'Camarosa' also can be grown in coastal southern California. Therefore, the new variety was tested against 'Camarosa' to determine if the new variety was distinct from 'Camarosa'.

1. The plant of the new variety is more vigorous with a higher number of adventitious crowns.

2. Fruit is larger and remains larger for a longer period through the harvest.

3. Fruit is conic in shape, as distinct from the wedge-shaped fruit of 'Camarosa'. The conical shape is relatively consistent throught the harvest period.

4. The taste and texture of the fruit after 7 days in cold storage is superior. A taste panel of 10 persons preferred 'NB -1' to 'Camarosa' 7 to 3 in a blind test when asked to compare overall palatability of fruits stored at 40 degrees Fahrenheit for 7 days in a commercial cooling facility after pre-cooling. Brilliant color of 'NB1' fruit is retained better in cold storage than that of 'Camarosa'.

5. The new variety is less susceptible to powdery mildew and interior crown rot.

6. Calyxes are larger and darker green those of 'Camarosa'. They tend to be flush with the outline of the fruit or slightly indented. Those of 'Camarosa' are often "necked", or bulging from the outline of the fruit.

7. Fruit of 'NB-1' is softer than that of 'Camarosa'. Tasters preferred the softer texture of 'NB-1' as "peach-like" as compared to "apple-like" firmness of 'Camarosa' fruit. Tasters rated the texture of 'NB-1' as more desirable in a dessert than that of 'Camarosa'.

8. 'NB-1' plants require less irrigation during fruiting season than 'Camarosa' plants.

TABLE 1

| Characteristic | NB-1 | Camarosa |
|---|---|---|
| leaf color | dark green | medium green |
| Munsell color | 7.5GY 4/4 | 5GY 4/3 |
| fruit size and shape | | |
| main season | large, conic | large, wedge/conic |
| early season | large, conic | large, "torpedo" |
| fruit exterior | color glossy red | glossy dark red |
| Munsell color | 5R 3/10 | 7.5R 4/11 |
| fruit interior color | slightly white | even dark red |
| Munsell color | 5R 6/10 | 7.5R 5/13 |
| inflorescence | very long, erect | long, semi-erect |
| fruit aroma | moderate | low |
| calyx position | even to indented | even to necked |

The new variety was grown side-by-side with 'Camarosa' in open field trials during the 1999–2000 growing season in Vista, Calif. The test plot is near sea level, on the coast of southern California.

Comparisons of the two varieties are based on the means of several observations. Field appearance ratings of the plants and fruits are based upon 7 positive observations of 'NB-1' to 5 positive observations of 'Camarosa'.

BRIEF DESCRIPTION OF THE ILLUSTRATIONS

The accompanying photographs show typical specimens of the new variety. FIGS. 1 and 2 were taken in the field under natural sunlight; FIGS. 3 through 9 were taken in a greenhouse under natural sunlight. All are in color as nearly true as was so reasonably possible.

DESCRIPTION OF THE NEW VARIETY

Figure 1:
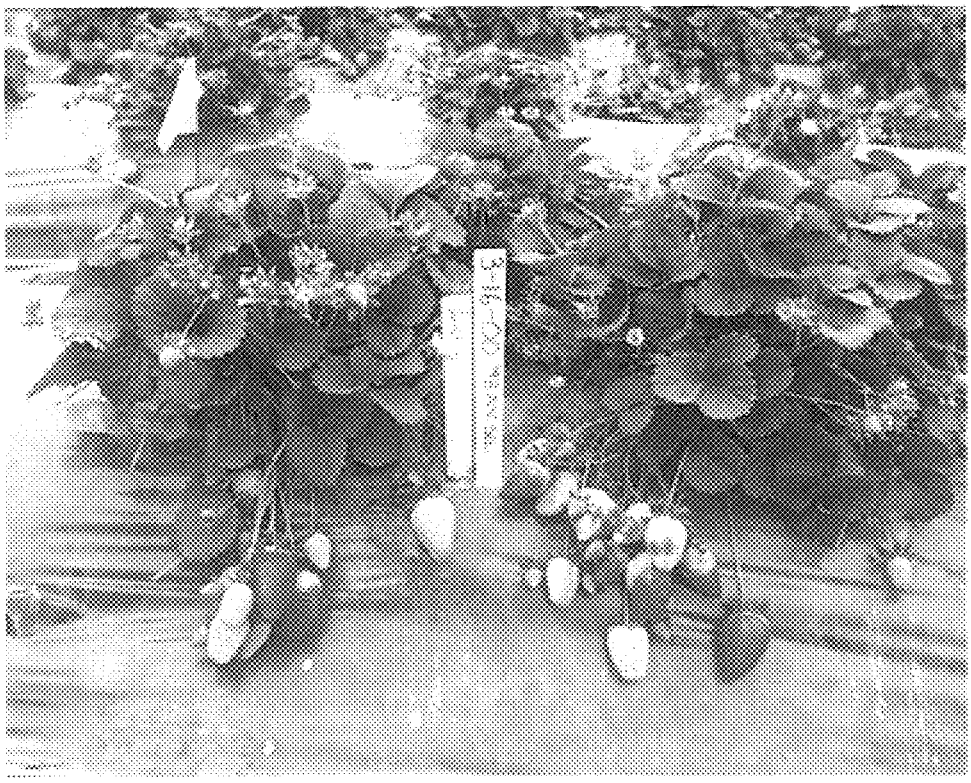
FIG. 1 represents the plant of the new variety at 174 days of age, with inflorescences and fruit in about the middle of the harvest season.
Figure 2:
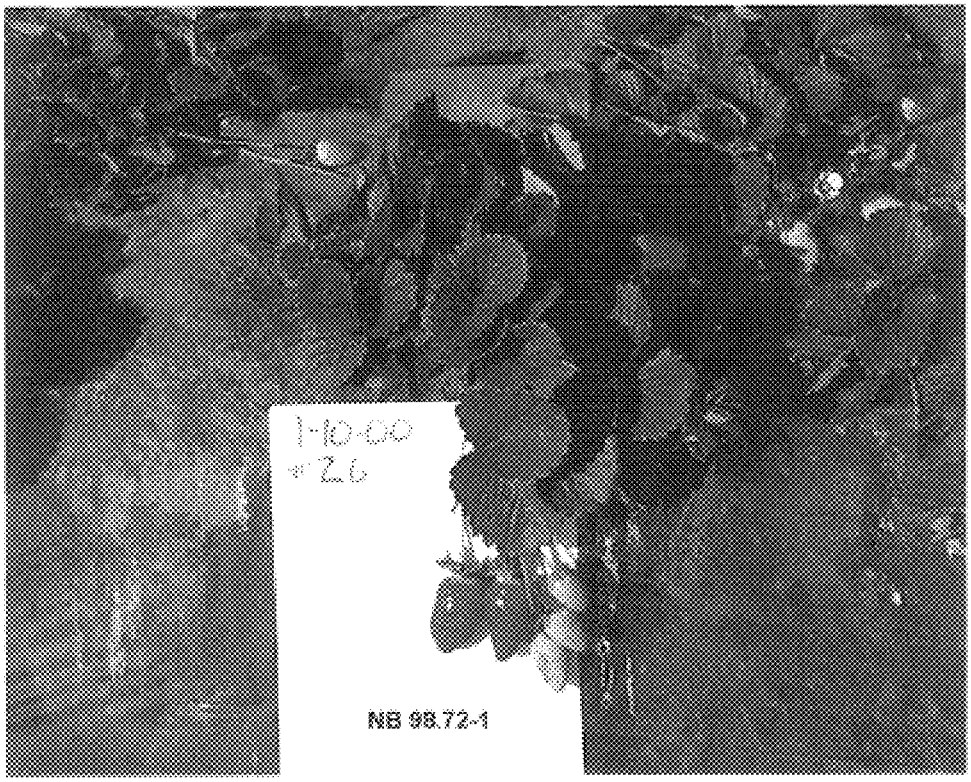
FIG. 2 represents the plant at 109 days age and fruit in early harvest season.
Figure 3:
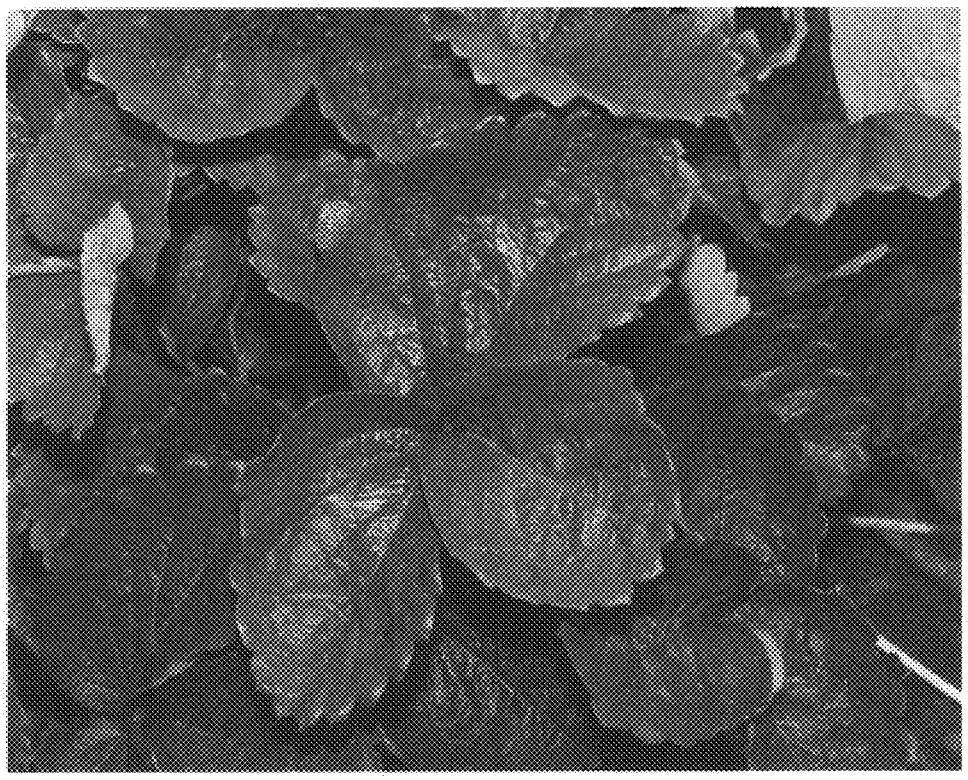
FIG. 3 represents a closer view of foliage of the new variety on a plant of 174 days of age.
Figure 4:
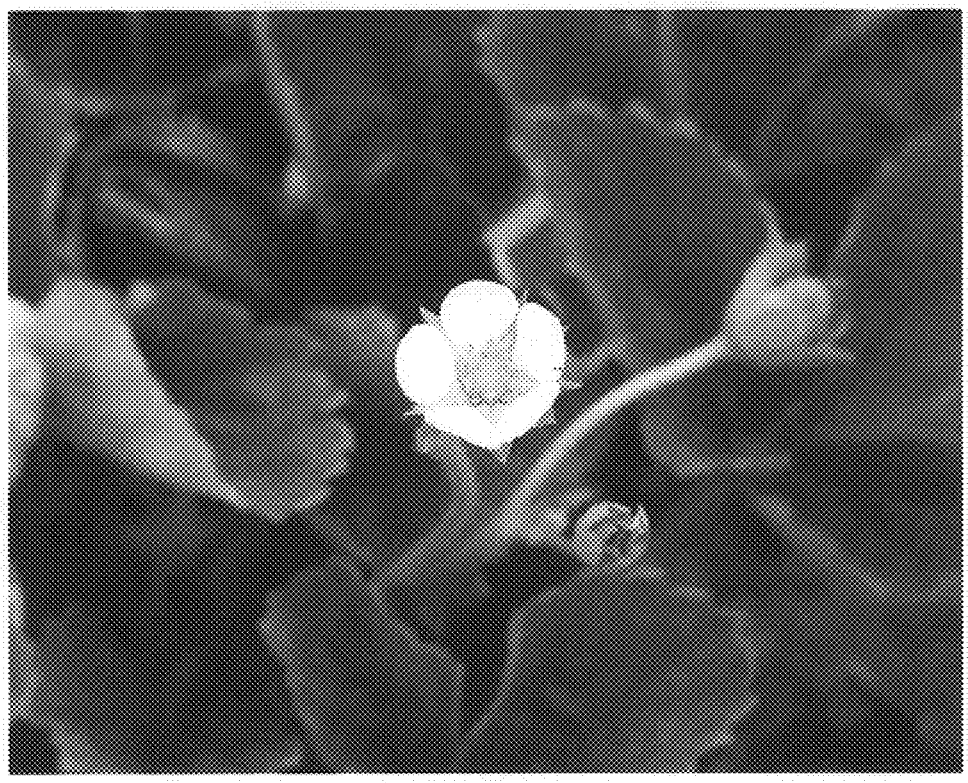
FIG. 4 represents the erect inflorescence of the plant of 174 days of age.
Figure 5:
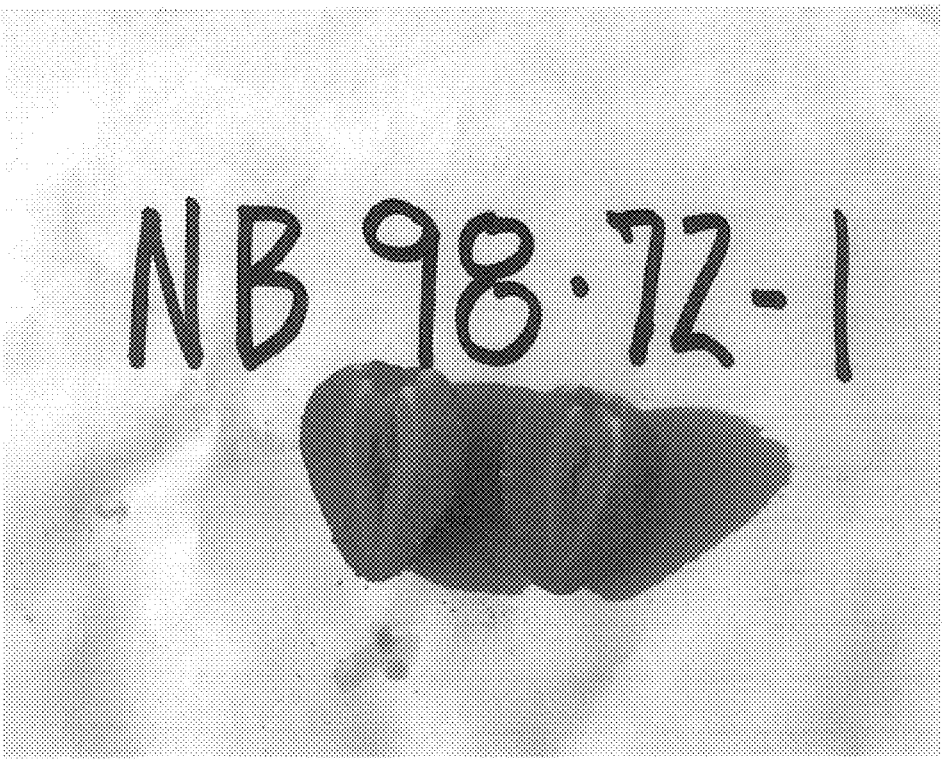
FIG. 5 represents a typical fruit, cut open to show the interior, taken from a plant 174 days of age.
Figure 6:
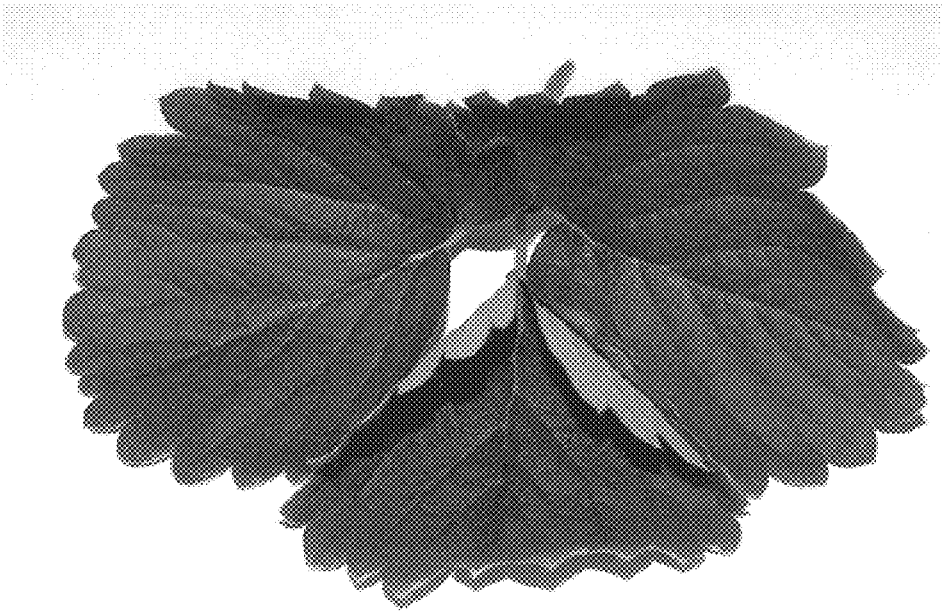
FIG. 6 represents a closer view of a single leaf of the new variety on a plant 174 days of age.
Figure 7:
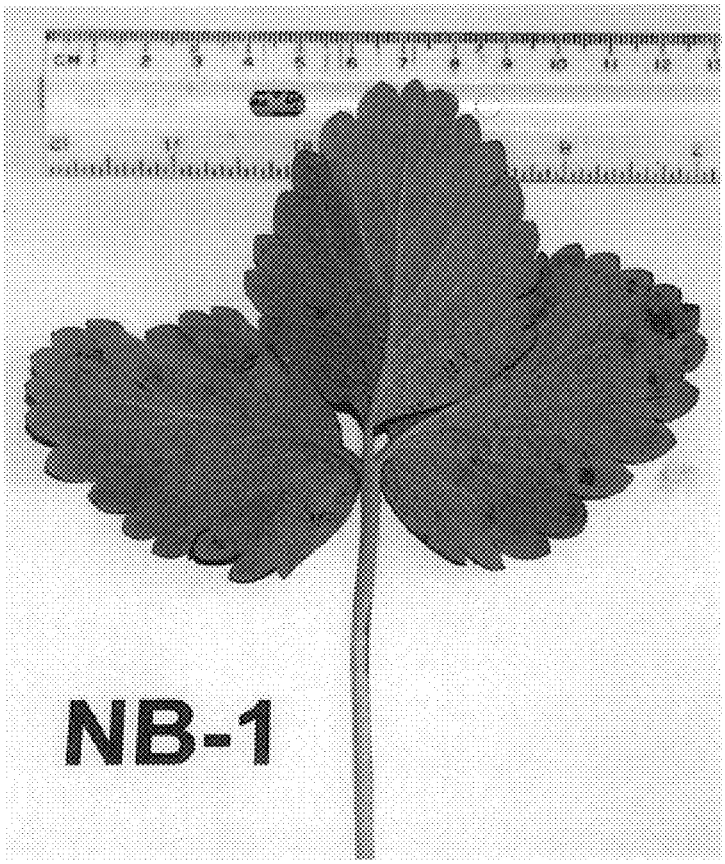
FIG. 7 represents lower surface to a leaf of a plant 185 days of age.
Figure 8:
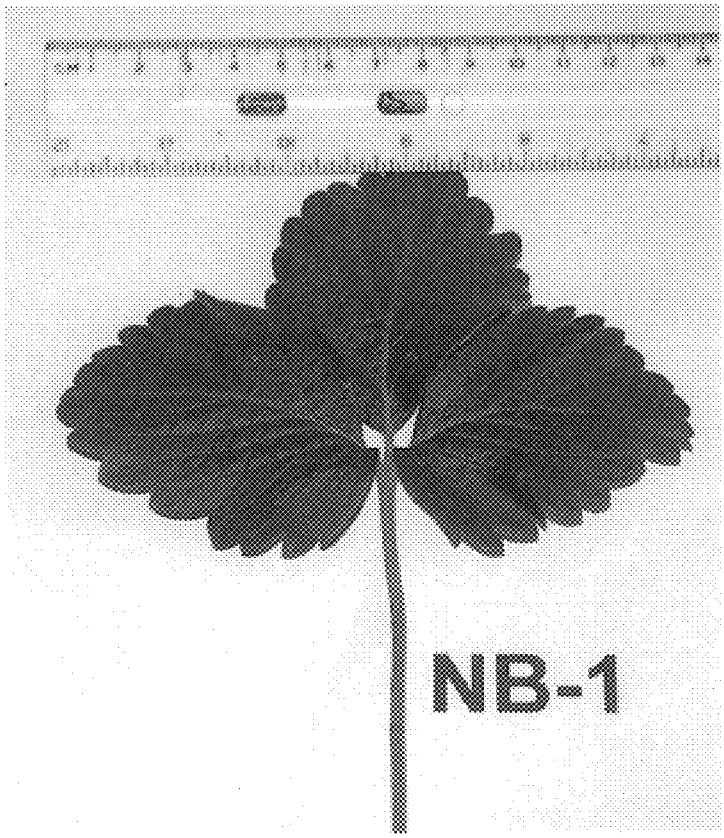
FIG. 8 represents the upper surface of a leaf of a plant 185 days of age.
Figure 9:
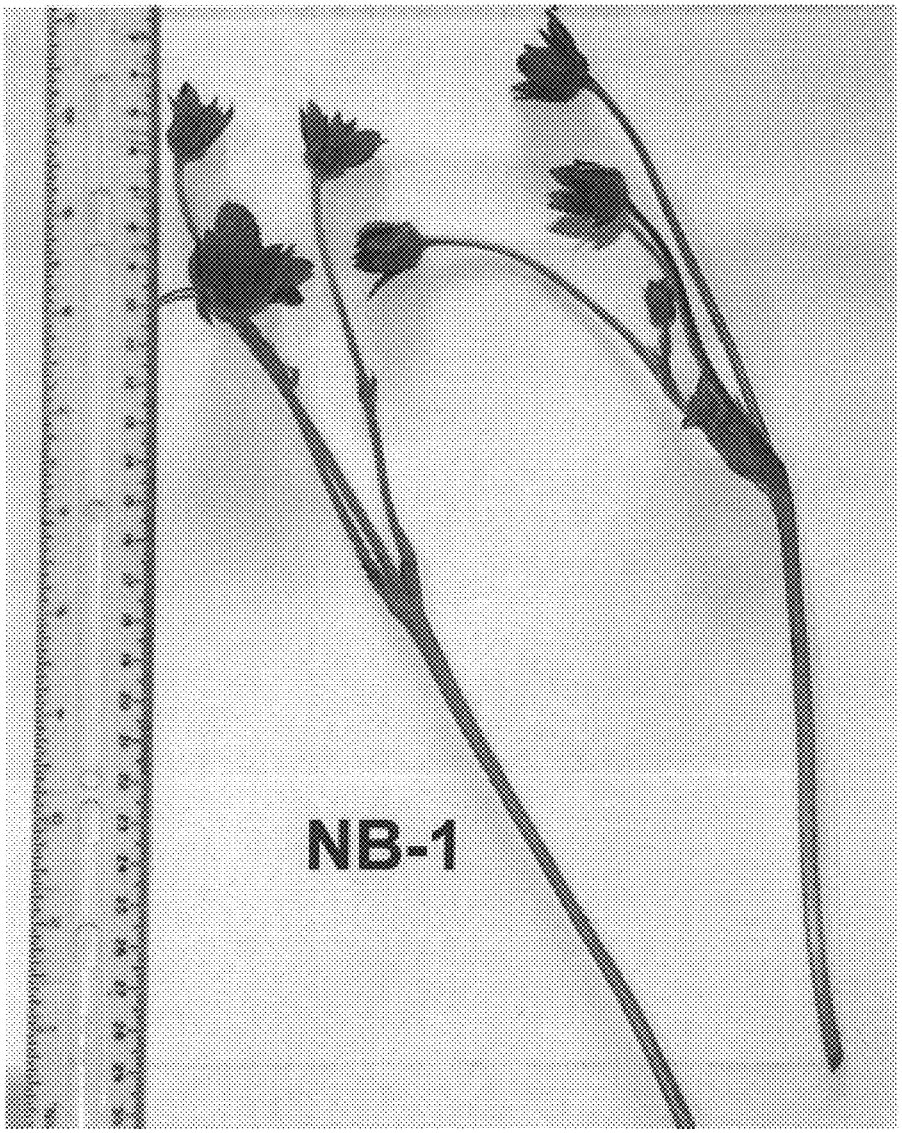
FIG. 9 represents two flower stalks of the late harvest period, showing double budding on a pedicel, from a plant 185 days of age.

The detailed description of the new variety is based upon observations made during production trials in open field conditions in Vista, Calif. during the 1999–2000 production season. Color, yield, size of plant parts, and other characteristics can vary, due to variation in the conditions of culture and environment.

Colors are designated both in standard terminology and in Munsell color classification notation. Munsell color classifications were done indoors under standard fluorescent lighting.

The following observations of the new variety were made on May 11, 2000 of plants 232 days old, planted out Sep. 23, 1999 in Vista, Calif.

Plant: The plants are erect and dense, globose in shape. Plants are generally 30 to 40 cm in diameter at time of harvest and average height of plants was 31 cm.

Root initiation: Primary adventitious roots arise from transplanted crowns in approximately 10 days with proper cultural care. Secondary roots arise within 5 days after transplanting. Secondary roots survive for a short period and are continually replaced during the growing season. The majority of root development is within the first 100 days after transplanting.

Stolons: Stolons from high elevation increase plots (Mcdoel Calif.) yield an average of 32 plants per mother plant. Low elevation increase plots (Oceanside, Calif.) yielded an average of 48 plants per mother plant. Stolons are very thick, with an average diameter of 0.6 cm. Midseason stolons are medium green in color, equivalent to Munsell 5 GY 6/10. On October 1, stolons were senescent and generally dark green to red in color. Pubesence is sparse and parallel to stolon.

Leaf: The average shape of the leaf is ovate trifoliate, with an average of 17 deep serrations per leaf. Mature leaves have very slight blistering near the main rib vein. The upper surface of the leaf is dark green, equivalent to Munsell 7.5GY 4/4; lower leaf color is 7.5 GF 8/4. The terminal leaflet has a mean length of 6.5 cm and a mean width of 6.2 cm. Average leaf dimensions are 8.8 cm by 8.1 cm. Lower leaf pubescence is moderately dense, 0.1 cm in length, and lies generally parallel to the leaf surface, pointing generally toward the petiole.

Petiole: The petiole is medium green, equivalent to Munsell 5GY 4/3. The petiole has a mean width of 3.25 cm and mean length of 17 cm. Pubescence is sparse to moderate on the main petiole, perpendicular, and 0.1 cm in length. At the trifoliate axis pubescence is very dense and downy.

Petiolule: Average length is 1.1 cm and average diameter at the widest part is 0.5 cm. Color is 5 GY7/6.

Leaf arrangement: The base angle of the terminal leaf blades is erect. Mature leaves are mostly flat, with an occasional concave leaf. Older senescent leaves tend to be convex. Bract leaflet position is erect. Bract leaflets commonly occur singly. Bract leaflet is elliptic in shape and parallel to the stolon.

Flower bud: Average dimensions just before opening are 1.2 cm diameter and length from base of bud to tip of sepal is 2.3 cm. Color is 7.5 GY 7/8. Pubescence is thick, downy, and perpendicular to bud.

Bloom: The inflorescence is very long, averaging 22 cm in length and is held erect at or above the leaves. The flowers are large, averaging 1.1 cm in diameter. There are six petals per flower. Average petal dimension is are 1.2 cm by 1.4 cm. Flowers are white. There is typically one flower per pedicel, but two flowers per pedicel may occur late in the harvest period. At mid-season, about 6 months after transplanting, inflorescence is typically 12 to 14 stalks per plant.

Sepals: 12 sepals per mature fruit. Average dimensions are 21. cm by 0.8 cm, with a lanceolate shape. Top of sepal is green equivalent to Munsell 7.5 GY 4/6; bottom is 7.5 GY 6/6. Calyx mean diameter is 6 cm. Attachment is flat to slightly indented.

Fruit: The fruit has a smooth exterior surface, glossy red in color (Munsell 5R 3/10). Internally, the fruit has some slightly white flesh, Munsell 5R 6/10. Achenes are red to light brown. They are mostly even, to indented. Fruit is large and conic in shape. Size remains nearly constant for a longer period than other varieties. The shape is very uniform and remains so throughout the harvest. Average mass of the fruit is 24.2 grams. Average dimensions are 6.7 cm by 5.4 cm. Fruit has a moderate aroma at room temperature. The fruit is slightly acidic. The taste is sweeter than that of 'Camarosa'. On a scale of 1–10, with 10 being very sweet, 'NB-1' as rated at 7 and 'Camarosa' at 4. Fruit is firm to the touch. After 7 days cold storage, fruit is slightly less firm; much less firm after warming to room temperature. On an scale of 1 to 10, with 10 being very firm, 'NB-1' rated at 4 after 7 days cold storage and return to room temperature. Fruit color remains brilliant after cold storage.

Yield: Average marketable harvest is 1376. grams per plant.

Culture: 'NB-1' is adapted to growing in open fields near the coast of southern California. It can be planted out in winter, has low chilling requirement, and sets fruit in short-day conditions. Plants are vigorous and relatively resistant to powdery mildew and interior crown rot. Requires less water during fruiting period than comparable varieties.

I claim:

1. A new and distinct variety of strawberry plant, substantially as described and depicted herein.

* * * * *